United States Patent [19]

Ballestrasse et al.

[11] 4,434,249

[45] Feb. 28, 1984

[54] METHOD OF PREPARING ACRYLIC ION-TRANSFER MEMBRANES

[75] Inventors: Cindy L. Ballestrasse, Seattle; Robert T. Ruggeri, Kirkland, both of Wash.

[73] Assignee: Electrochemical Technology Corp., Seattle, Wash.

[21] Appl. No.: 392,731

[22] Filed: Jun. 28, 1982

[51] Int. Cl.³ .............................................. B01J 47/12
[52] U.S. Cl. .................................... 521/27; 526/288; 526/307; 526/317
[58] Field of Search ........................................... 521/27

[56] References Cited

U.S. PATENT DOCUMENTS

| | | | |
|---|---|---|---|
| 2,567,836 | 9/1951 | Anthes | 260/89.7 |
| 2,980,657 | 4/1961 | Melamed | 260/86.1 |
| 3,718,500 | 2/1973 | Nyquist | 117/132 R |
| 3,725,291 | 4/1973 | Serbas | 521/28 |
| 4,009,201 | 2/1977 | Steckler et al. | 526/316 |
| 4,139,684 | 2/1979 | Coupek et al. | 521/27 |

Primary Examiner—Joseph L. Schofer
Assistant Examiner—Peter F. Kulkosky
Attorney, Agent, or Firm—Merriam, Marshall & Bicknell

[57] ABSTRACT

Ion exchange resins can be prepared by co-polymerizing a major amount (>88 mol %) of non-ionic acrylic monomer, such as methyl methacrylate, with a minor amount (3 to 12 mol %) of an ionogenous monomer such as methacrylamidopropyltrimethylammonium chloride or 2-acrylamido-2-methyl propane sulfonic acid. The resultant anion-conductive or cation conductive membranes exhibit low swelling in water and high ion-transference numbers. The membranes may be applied as coatings on neural prosthesis electrodes.

22 Claims, 6 Drawing Figures

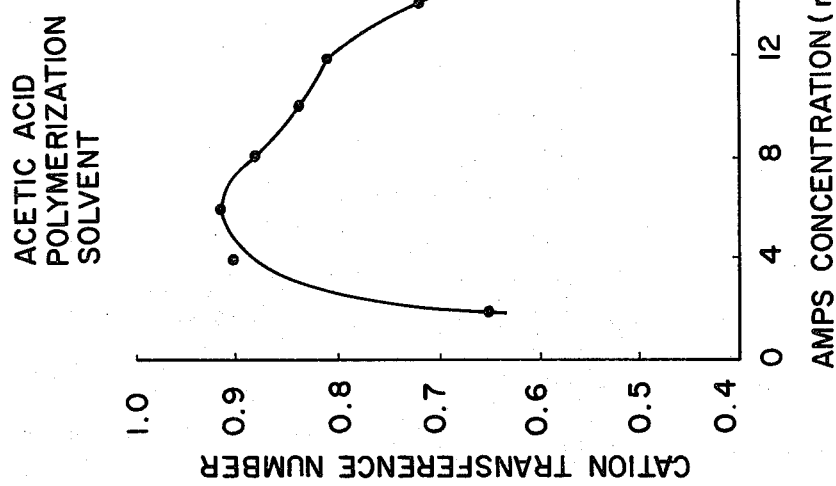
FIG. 5 ACETIC ACID POLYMERIZATION SOLVENT
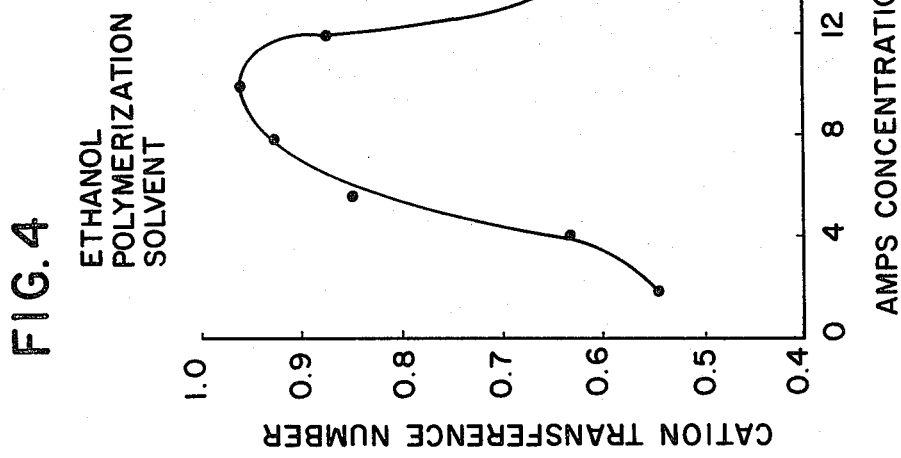
FIG. 4 ETHANOL POLYMERIZATION SOLVENT

METHOD OF PREPARING ACRYLIC ION-TRANSFER MEMBRANES

BACKGROUND OF THE INVENTION

The U.S. Government has a paid-up license in this invention and the right in limited circumstances to require the patent owner to license others on reasonable terms as provided for by the terms of contract No. NIH-N01-NS-0-2316 awarded by the National Institute of Health.

The present invention relates to ion-transfer (ion-exchange) membranes and methods of preparing such membranes from acrylic monomers. Both cation-conductive and anion-conductive membranes can be prepared, depending on the nature of the monomers utilized.

The membranes of the instant invention are copolymers of at least two acrylic monomers. The major monomeric component (>88 mol %) is a non-ionic, hydrophobic material such as methyl methacrylate (MMA). The other essential monomeric ingredient comprises 3 to 12 mol % of an acrylic monomer which contains ionogenous groups, e.g., methacrylamidopropyltrimethylammonium chloride (MAPTAC), dimethylaminopropyl methacrylamide (DMAPMA) or 2-acrylamido-2-methyl propane sulfonic acid (AMPS). Other materials, such as crosslinkers, and polymerization initiators can also be employed.

These copolymers are inexpensive, easily made, and form strong, resilient membranes. One application of such membranes is as coatings for neural prosthesis electrodes formed of silver. Because silver ions are toxic to neural tissue, an anion-conducting membrane coating is necessary to prevent silver ions from migrating into the body tissue while still allowing chloride ions to carry the current.

The membranes of the present invention also have utility in a number of fields where existing ion-exchange resins are now used. Examples of these fields are water purification by ion-exchange or electrodialysis, purification or modification of foodstuffs or pharmaceuticals by ion-exchange or electrolysis, and uses in chemical processing and battery technologies.

Most commercial ion-exchange resins described in the literature have a polystyrene backbone. These resins are synthesized through a complex reaction sequence, and utilize toxic chlorinated aromatic intermediates. In the instance of membranes intended for use as coatings for surgically-implanted devices, toxic residue remaining in the electrode cannot be tolerated.

In conventional ion-exchange materials high transference numbers are achieved because Donnan exclusion prevents co-ions from entering the polymer membrane. Furthermore, the Donnan exclusion is enhanced by a high concentration of fixed charges in the membrane, i.e., high ion-exchange capacity. Commercial ion-exchange membranes generally have ion-exchange capacities greater than 1 meq/g.

The primary properties desired in an ion-exchange membrane are: (1) High transference number, (2) high conductivity, (3) low swelling, (4) high mechanical toughness and strength, and (5) low electroosmosis.

Some of these properties are incompatible with each other. Conventional membranes achieve both high transference numbers and high conductivity by increasing the ion-exchange capacity, but this increases swelling. If swelling is minimized by using a high concentration of cross-linking agent, the membrane becomes brittle. Membranes used to coat prosthesis electrodes require high transference numbers ($t > 0.95$), high conductivities ($\kappa > 10^{-3} \Omega^{-1} cm^{-1}$), minimal swelling ($S < 2.0$), and small thickness ($\tau = 1$ to $50$ $\mu m$). Conventional ion exchange membranes are cast in relatively thick films (typically $\tau = 0.5$ to $2.0$ mm) in order to achieve good mechanical strength.

New membranes are conventionally made by polymerizing the monomers under oxygen-free conditions. Oxygen can be excluded by polymerizing the resin between sheets of glass.

The use of acrylic monomers containing ionogenous groups to form an ion-exchange material has been recognized in the prior art, i.e., U.S. Pat. No. 4,139,684, to Coupek, et al. This patent, however, does not deal with membranes but with gel-like materials. Unlike the compositions of the present invention which contain a major amount of a hydrophobic species such as MMA, the foregoing patent suggests that a hydrophilic monomer is essential. Moreover, one of the properties of the copolymers of the present invention is that satisfactory membranes can be formed without the use of an added cross-linker. In contrast, the compositions of the U.S. Pat. No. 4,139,684 patent require a large amount of cross-linker ($\geq 30\%$).

Another patent of interest to the background of the present invention is U.S. Pat. No. 3,718,500 to Nyquist which discloses and claims adherent coatings for non-porous substrates, formed from copolymers of alkyl amino alkyl acrylamides and monoethylenically unsaturated monomers. Although some of the materials disclosed by the U.S. Pat. No. 3,718,500 are similar to those utilized to form the membranes of the present invention, there is no teaching or suggestion in the referenced patent that these coatings have any appreciable conductivity, ion-transporting ability, or that a membrane could be formed therefrom.

BRIEF DESCRIPTION OF THE DRAWINGS

FIGS. 1 through 6 are graphs illustrating the physical properties of membranes formed by co-polymerizing an ionogenous monomer and a non-ionic, acrylic hydrophobe. The figures show the relationship of various physical properties to the level of ionogenous material in the copolymer.

FIG. 1 illustrates changes in the swelling ratio as a function of MAPTAC concentration for membranes formed from MAPTAC (methacrylamidopropyltrimethylammonium chloride) and MMA (methyl methacrylate), utilizing TMA (tetramethylene glycol dimethacrylate) as a cross-linker. The membrane polymerizations were carried out in ethanol solvent;

FIG. 2 illustrates the relationship of membrane conductivity to MAPTAC concentration for the MAPTAC/MMA membranes of FIG. 1;

FIG. 3 illustrates changes in anion transference number as a function of MAPTAC concentration for the MAPTAC/MMA membranes of FIG. 1;

FIG. 4 illustrates changes in cation transference number as a function of the level of ionogenous monomer for membranes formed of copolymers of AMPS (2-acrylamido-2-methyl propane sulfonic acid) and MMA. The polymerization was carried out in an ethanol solvent;

FIG. 5 illustrates the cation transference number for AMPS/MMA membranes prepared using an acetic acid polymerization solvent; and FIG. 6 illustrates changes in anion transference number as a function of the level of ionogenous monomer for membranes formed of copolymers of DMAPMA (dimethylaminopropyl methacrylamide) and MMA. The polymerization was carried out in ethanol solvent.

DETAILED DESCRIPTION

The ion-transfer membranes of the present invention comprise co-polymers of at least two acrylic monomers. The major monomeric component (>88 mol %, based on the total amount of reactant monomers) is a non-ionic, hydrophobic acrylate having the formula:

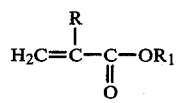

where R is H or $CH_3$ and $R_1$ is methyl, ethyl or butyl.

The other essential monomeric ingredient comprises 3 to 12 mol % of an acrylic monomers which contains ionogenous groups. Examples of such materials include acrylic acid, methacrylic acid, or monomers represented by the formula:

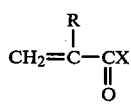

wherein:
R is H or $CH_3$,
and X is

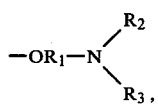

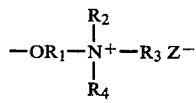

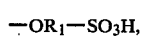

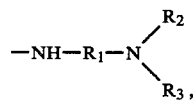

$-NH-R_1-SO_3H$, or

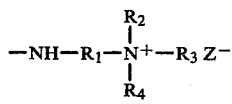

$R_1$ is alkylene or hydroxyalkylene,
$R_2$, $R_3$ and $R_4$ are hydrogen, alkyl, hydroxyalkyl
$Z^-$ is a halide, acetate, or methyl sulfate ion.

The polymerization reaction can be performed in a variety of organic solvents. It is generally desirable, however, for the organic solvent to have some appreciable solubility in water. Water soluble organic acids and alcohols are thus particularly useful. Polymerization solvents which are especially preferred in the process are ethanol or acetic acid, in concentrations from about 50 to about 300 mol %. The molar concentration of the hydrophobic monomer should be in the range 2.5 to 7.5 molar and the molar concentration of ionogenous monomer in the range of 0.10 to 0.75 molar. Membranes can also be formed using mixtures of monomeric ingredients, e.g., MMA/BMA/MAPTAC/DMAPMA, as long as the total amounts of hydrophobic and ionogenous monomers in the reaction mixture are within the foregoing molar concentration ranges.

Reaction temperatures from about 55° to 80° C. can be used, with 75° C. being most preferable. Polymerization proceeds via a free radical process, and any of the polymerization initiators conventionally utilized to form polymethyl methacrylates may be employed. The preferred polymerization initiator is 0.088 mol % azobisisobutyronitrile (AIBN).

The resin can be prepared in bulk form by polymerizing the reaction mixture in a suitable closed vessel such as a stoppered test tube. The resin can be prepared in sheet form by polymerizing between glass plates. The latter form is useful for measuring electrical properties of conductivity and transference number in the well known Hittorf cell.

It has been found that effective membranes can be prepared which comprise the non-cross-linked co-polymer itself and that there is no necessity to employ a cross-linking agent. However, if desired, the copolymer can also include up to about 5 mol % of a divinyl cross-linking agent such as tetramethylene glycol dimethacrylate (TMA), with 2.5% TMA being prefered.

Figure 1:
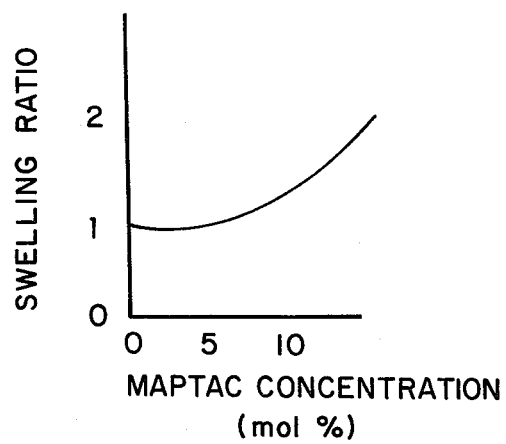
Figure 2:
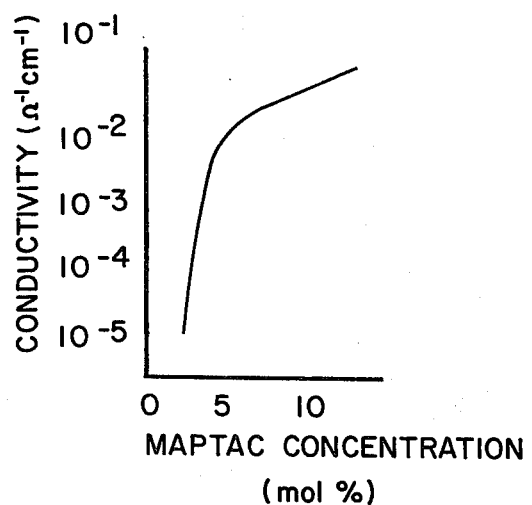
Figure 3:
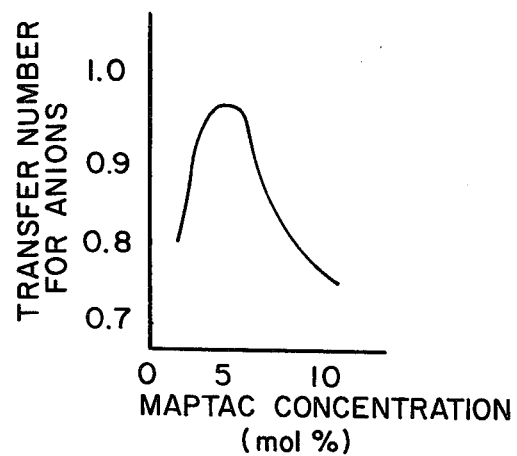

The properties of an ion-transfer membrane, formed in accordance with the method of the present invention by copolymerizing methylacrylamidopropyltrimethylammonium chloride (MAPTAC) and methyl methacrylate (MMA) in ethanol solvent, are illustrated in FIGS. 1 to 3.

Surprisingly, the data indicate that there is an optimum concentration level of ionogenous monomer for maximum transfer of ions across the membrane. A relatively small departure from the optimum level in either direction will result in a decrease in transference number. This situation is illustrated in FIG. 3 for a MAPTAC/MMA membrane. Measurements were made by placing the membranes in a Hittorf cell with a sodium chloride solution on either side of the membrane. The concentration of NaCl on one side of the cell was kept constant, but varied on the other side. Potential differences were measured and the transference number determined from the potential difference and the ratio of the activities. At the optimum MAPTAC concentration, near 4 mol %, the maximum transference number for anions was obtained in sodium chloride solution. The transference number for the anion, chloride, is the fraction of the current carried by that ion.

Anion transference numbers for resins in the range of 4 to 6 mol % MAPTAC have been in the range of 0.90 to 0.99, with a mean of about 0.96, using the foregoing potential difference method with a Hittorf cell. When a more accurate method was utilized, employing a radiotracer ($Na^{22}$) in a Hittorf cell, transference numbers of 0.999 were observed.

Conductivity increases with MAPTAC concentration (FIG. 2) and is at a satisfactory level for use as an electrode coating at 4 mol % MAPTAC. As shown in FIG. 1, swelling ratio, which is defined as the weight of the resin when swollen in water divided by the original weight, is near unity for compositions of 0 to 5 mol % MAPTAC but increases rapidly with mol % MAPTAC above the 5 mol % level. The ion-exchange capacity of a resin with 4 mol % MAPTAC is about 0.4 meq/g of dry material. Although the membranes of FIGS. 1 to 3 were formed in an ethanol solvent, similar results were obtained using acetic acid solvent.

FIGS. 4 and 5 show the changes in cation transference number resulting from varying the level of ionogeneous monomer in AMPS/MMA membranes. Copolymers of AMPS/MMA were made in both ethanol and acetic acid polymerization-solvents. Membranes made in ethanol had peak selectivity at 10 mol % AMPS (FIG. 5). The membrane's cation transference at this concentration was 0.96. Swelling ratio and conductivity for the ethanol-polymerized species at the 10 mol % AMPS level were 1.5 and $4 \times 10^{-4}$ $\Omega^{-1}$cm$^{-1}$, respectively.

AMPS/MMA membranes polymerized in acetic acid exhibited a peak selectivity at 6 mol % AMPS (FIG. 5). The cation transference number at this concentration was 0.91. Swelling ratio and conductivity were 1.1 and $5 \times 10^{-5}$ $\Omega^{-1}$cm$^{-1}$, at this level.

Figure 6:
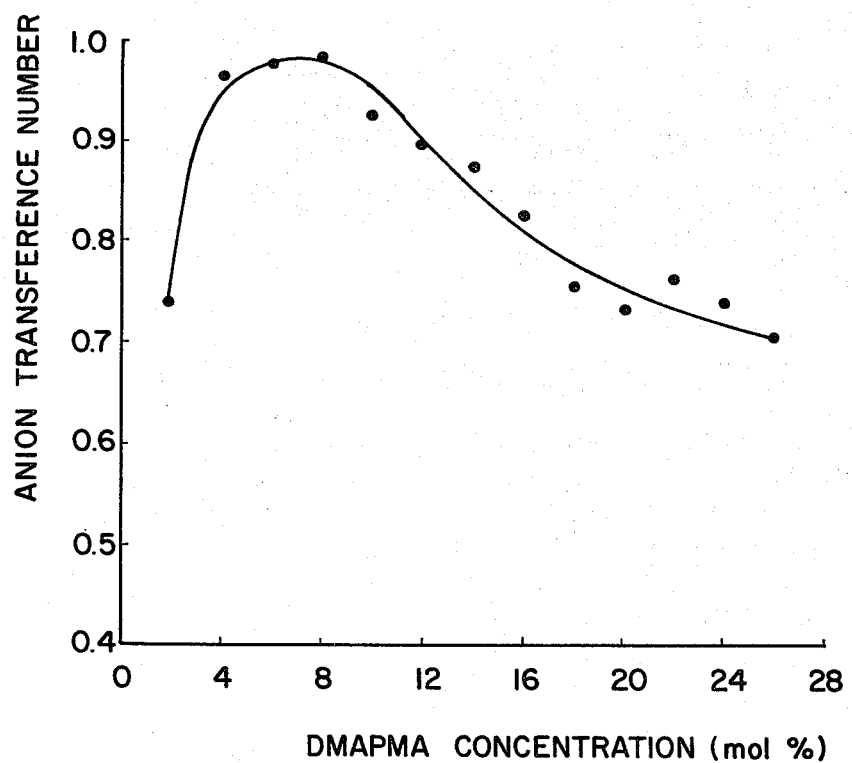

FIG. 6 shows changes in anion transference number for DMAPMA/MMA membranes. The membranes of FIG. 6 were made in ethanol solvent and exhibited a peak anion transference number of 0.98 at about 8 mol % DMAPMA. The conductivity at this level is $3 \times 10^{-4} \Omega^{-1}$cm$^{-1}$, and the swelling ratio is 0.85.

For the anion-conducting membrane formed from MAPTAC/MMA, optimum properties in terms of anion transference number are encountered when the ionogenous MAPTAC material is present at about 4 to 6 mol %. Other materials exhibit different optimums. Although the optimum concentration range for membranes fabricated in accordance with the procedures of the present invention will vary, depending on the particular monomers and solvents utilized, it has been found that satisfactory membrane properties result when the level of the ionogenous material is in the range 3 to 12 mol %. The optimum level of ionogenous monomer for any particular system will lie in a somewhat narrower range between 3 to 12%, i.e., 4 to 6 mol % for MAPTAC/MMA.

There may be situations, however, where high transference is not necessary for the particular membrane application. In that event, higher levels of ionogenous monomer may be utilized in formulating the membranes. Indeed, there may exist some applications where a lower transference number (and a higher level of ionogenous monomer) may be desirable.

Electrodes can be coated with a protective membrane by dipping the electrode into the monomer reaction mixture and heating the coated electrode in an oxygen-free atmosphere. In view of the fact that the unreacted monomer mixture is generally of low viscosity, there exists the possibility of voids in the membrane coating due to flow of the non-viscous coating. The preferred method of coating electrodes, therefore, is as follows. A mixture comprising an ionogenous acrylic monomer and a non-ionic, hydrophobic acrylic monomer (e.g., MAPTAC/MMA) in a solvent is partially polymerized in an inert atmosphere at about 75° C. until the viscosity increases to a syrupy consistency. The mixture is quenched to room temperature to stop the polymerization. Electrodes are dipped into this viscous mixture and withdrawn. The adherent film of partially polymerized material is then cured in a nitrogen atmosphere at 75° C., forming an ion-exchange membrane barrier on the electrode.

Membranes can also be prepared by use of a mold. One method of such preparation is by polymerizing the monomer mixture in the cavity between two or more glass sheets separated by a ring-shaped rubber gasket. A solution of the monomer mixture in ethanol or other solvent is injected through the rubber gasket into the void betweens the plates. As the void fills with monomer solution, the displaced air is permitted to escape through a vent. Once the void between the glass plates has filled with monomer, the rubber gasket is sealed to prevent the ingress of air. The monomer-containing glass plates are cured in an oven at 75° C. for 24 hours. The resultant films are flexible and rubbery upon removal from the glass plates and became tough and hard upon evaporation of the solvent.

When employed in an industrial application, one or more rubbery membranes are mounted in combination with porous support sheets in a plate and frame assembly, a membrane lined tube, a spiral wound cylinder, or other conventional ion exchange apparatus.

EXAMPLE 1

A mixture of 0.84 ml of 50 weight % aqueous MAPTAC (0.0020 moles MAPTAC, 0.025 moles water), 3.33 ml MMA (0.0314 moles), 2.0 ml ethanol (0.0343 moles), 0.194 ml TMA (tetramethylene glycol dimethacrylate)($8.70 \times 10^{-4}$ moles), and 0.165 ml of a 0.183 M solution of AIBN (azobisisobutyronitrile) in ethanol ($3.01 \times 10^{-5}$ moles AIBN) was prepared in a test tube. The test tube was sealed with a cork and heated in a 75° C. oven for 24 hours. The resultant polymer was flexible and rubbery when removed from the test tube and became tough and hard upon evaporation of the solvent.

EXAMPLE 2

A mixture of 0.266 g AMPS (2-acrylamido-2-methyl propane sulfonic acid, 0.00128 moles), 1.227 ml MMA (0.0116 moles), 0.75 ml ethanol (0.0128 moles), 0.284 ml water (0.0158 moles), and 0.093 ml of a 0.122 M solution of AIBN in ethanol ($1.13 \times 10^{-5}$ moles AIBN) was prepared in a test tube. The test tube was sealed with a cork and heated in a 75° C. oven for 24 hours. The resultant polymer was flexible and rubbery when removed from the test tube and became tough and hard upon evaporation of the solvent.

EXAMPLE 3

A mixture of 0.186 ml DMAPMA (dimethylaminopropyl methacrylamide, 0.00103 moles), 1.255 ml MMA (0.0118 moles), 0.75 ml ethanol (0.0128 moles), 0.227 ml water (0.0126 moles), and 0.093 ml of a 0.122 M solution of AIBN in ethanol ($1.13 \times 10^{-5}$ moles AIBN) was prepared in a test tube. The test tube was sealed with a cork and heated in 75° C. oven for 24 hours. The resultant polymer was flexible and rubbery when removed form the test tube and became tought and hard upon evaporation of the solvent.

EXAMPLE 4

A mixture of 1.00 ml of 50 weight % aqueous MAPTAC (0.00238 moles MAPTAC, 0.0292 moles water), 4.67 ml EMA (ethyl methacrylate, 0.0373 moles), 2.64 ml ethanol (0.0452 moles), 0.23 ml TMA (0.00101 moles), and 0.29 ml of a 0.122 M solution of AIBN in ethanol ($3.50 \times 10^{-5}$ moles AIBN) was prepared in a test tube. The test tube was sealed with a cork and heated in a 75° C. oven for 24 hours. The resultant polymer was flexible and rubbery when removed from the test tube and became harder, but still retained some rubberiness upon evaporation of the solvent.

EXAMPLE 5

A mixture of 1.49 ml of 50 weight % aqueous MAPTAC (0.00355 moles MAPTAC, 0.0435 moles water), 6.45 ml BMA (butyl methacrylate, 0.0408 moles), 7.97 ml ethanol (0.137 moles), 0.26 ml TMA ($1.16 \times 10^{-3}$ moles), and 0.33 ml of a 0.122 M solution of AIBN in ethanol ($4.00 \times 10^{-5}$ moles AIBN) was prepared in a test tube. The test tube was sealed with a cork and heated in a 75° C. oven for 24 hours. The resultant polymer was soft and rubbery.

EXAMPLE 6

The monomer mixtures of Examples 1–5 were prepared. Instead of polymerizing the mixtures in test tubes, however, each of the monomer mixtures was cast into membranes in accordance with the following procedure. Several glass plates were clamped together with a rubber ring separating adjacent plates. Monomer mixture was injected through the rubber ring into the disc-shaped void with a syringe. Air escaped through a second needle as the void filled with monomer solution. After the needles were removed, the entire stack was placed in the 75° C. oven for 24 hours to polymerize. The resultant films were flexible and rubbery after removal from the mold and became tough and hard upon evaporation of the solvent.

What is claimed:

1. A process for forming ion-transfer membranes which comprises the following steps in sequence:
   preparing a reaction mixture consisting essentially of:
   (A) a major, non-ionic component selected from the group consisting of a hydrophobic acrylic monomer having the formula:

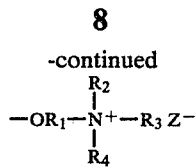

where R is H or $CH_3$ and $R_1$ is methyl, ethyl or butyl, and mixtures of two or more of said hydrophobic monomers;
   (B) a minor, ionogenous acrylic monomer component selected from the group consisting of: (i) acrylic acid; (ii) methacrylic acid; (iii) monomers represented by the formula:

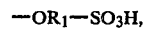

wherein:
   R is H or $CH_3$,
   and X is

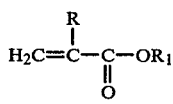

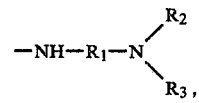

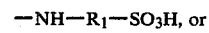

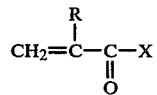

—NH—$R_1$—$SO_3H$, or

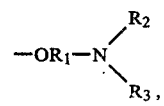

$R_1$ is alkylene or hydroxyalkylene
   $R_2$, $R_3$ and $R_4$ are hydrogen, alkyl, or hydroxyalkyl, and
   $Z^-$ is a halide, acetate, or methyl sulfate ion; and, (iv) mixtures of two or more of said ionogenous acrylic monomers; and
   (C) an organic solvent,
   wherein the concentration of said major, non-ionic component in said solvent is in the range 2.5 to 7.5 molar, and the concentration of said minor, ionogenous component in said solvent is in the range 0.10 to 0.75 molar, and wherein the molar concentration of said ionogenous component is between 3 and 12% of the total monomer content in said reaction mixture;
   depositing a thin film of said reaction mixture on a substrate; and
   heating said deposited film in a substantially oxygen-free environment at a temperature between 55 degrees C. and 80 degrees C.

2. The process of claim 1 wherein said organic solvent is a water soluble alcohol.

3. The process of claim 1 wherein said organic solvent is a water soluble acid.

4. The process of claim 1 wherein said organic solvent is selected from the group consisting of ethanol and acetic acid.

5. The process of claim 1 wherein said reaction mixture further includes a polymerization initiator.

6. The process of claim 1 wherein said reaction mixture further includes a cross-linker.

7. The process of claim 5 wherein said polymerization initiator is azobisisobutyronitrile.

8. A process for forming ion-transfer membranes which comprises the following steps in sequence:
   preparing a reaction mixture consisting essentially of:
   (A) a major, non-ionic component selected from the group consisting of a hydrophobic acrylic monomer having the formula:

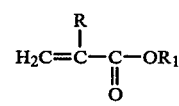

where R is H or $CH_3$ and $R_1$ is methyl, ethyl or butyl, and mixtures of two or more of said hydrophobic monomers;

(B) a minor, ionogenous acrylic monomer component selected from the group consisting of: (i) acrylic acid; (ii) methacrylic acid; (iii) monomers represented by the formula:

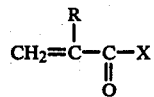

wherein:
R is H or CH₃,
and X is

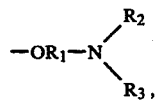

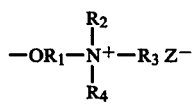

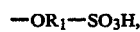

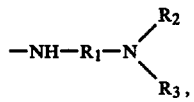

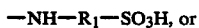

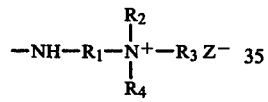

R₁ is alkylene or hydroxyalkylene
R₂, R₃ and R₄ are hydrogen, alkyl, or hydroxyalkyl, and
Z⁻ is a halide, acetate, or methyl sulfate ion; and, (iv) mixtures of two or more of said ionogenous monomers; and
(C) an organic solvent,
wherein the concentration of said major, non-ionic component in said solvent is in the range 2.5 to 7.5 molar, and the concentration of said minor, ionogenous component in said solvent is in the range 0.10 to 0.75 molar, and wherein the molar concentration of said ionogenous component is between 2 and 12% of the total monomer content in said reaction mixture;
heating said reaction mixture to a viscous consistency at a temperature between 55 and 80 degrees C. in a substantially oxygen-free environment;
coating a substrate with a film of said viscous reaction mixture; and
heating said deposited film to a temperature between 55 and 80 degrees C. in a substantially oxygen-free environment until said film becomes rubbery.

9. A process for forming ion-transfer membranes which comprises the following steps in sequence
preparing a reaction mixture consisting essentially of:
(A) a major, non-ionic component selected from the group consisting of a hydrophobic acrylic monomer having the formula:

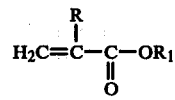

where R is H or CH₃ and R₁ is methyl, ethyl or butyl and mixtures of two or more of said hydrophobic monomers;
(B) a minor, ionogenous acrylic monomer component selected from the group consisting of: (i) acrylic acid; (ii) methacrylic acid; (iii) monomers represented by the formula:

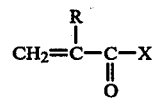

wherein:
R is H or CH₃,
and X is

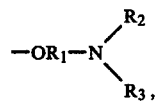

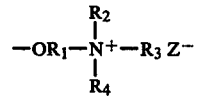

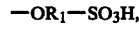

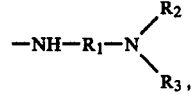

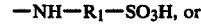

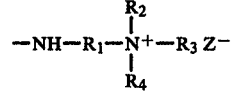

R₁ is alkylene or hydroxyalkylene
R₂, R₃ and R₄ are hydrogen, alkyl, or hydroxyalkyl, and
Z⁻ is a halide, acetate, or methyl sulfate ion; and, (iv) mixtures of two or more of said ionogenous monomers; and
(C) an organic solvent,
wherein the concentration of said major, non-ionic component in said solvent is in the range 2.5 to 7.5 molar, and the concentration of said minor, ionogenous component in said solvent is in the range 0.10 to 0.75 molar, and wherein the molar concentration of said ionogenous component is between 3 and 12% of the total monomer content in said reaction mixture;
introducing a quantity of said reaction mixture into a mold cavity and thereafter maintaining said mold cavity in a substantially oxygen-free condition;
heating said mold cavity to a temperature between 55 and 80 degrees C. and maintaining said temperature until the mold cavity contents becomes rubbery; and removing said rubbery contents from said mold cavity.

10. The process of claim 1, 8, or 9, wherein said ionogenous monomer is methacrylamidopropyltrimethylammonium chloride.

11. The process of claim 8 wherein said organic solvent is a water soluble alcohol.

12. The process of claim 8 wherein said organic solvent is a water soluble acid.

13. The process of claim 8 wherein said organic solvent is selected from the group consisting of ethanol and acetic acid.

14. The process of claim 8 wherein said reaction mixture further includes a polymerization initiator.

15. The process of claim 8 wherein said reaction mixture further includes a cross-linker.

16. The process of claim 8 wherein said polymerization initiator is azobisisobutyronitrile.

17. The process of claim 9 wherein said organic solvent is a water soluble alcohol.

18. The process of claim 9 wherein said organic solvent is a water soluble acid.

19. The process of claim 9 wherein said organic solvent is selected from the group consisting of ethanol and acetic acid.

20. The process of claim 9 wherein said reaction mixture further includes a polymerization initiator.

21. The process of claim 9 wherein said reaction mixture further includes a cross-linker.

22. The process of claim 9 wherein said polymerization initiator is azobisisobutyronitrile.

* * * * *